United States Patent [19]

Chang et al.

[11] Patent Number: 5,089,603

[45] Date of Patent: * Feb. 18, 1992

[54] ANTIGENIC EPITOPES PRESENT ON MEMBRANE-BOUND BUT NOT SECRETED IGA

[75] Inventors: Tse-wen Chang; Nancy T. Chang, both of Houston, Tex.

[73] Assignee: Tanox Biosystems, Inc., Houston, Tex.

[*] Notice: The portion of the term of this patent subsequent to Jan. 7, 2009 has been disclaimed.

[21] Appl. No.: 455,080

[22] Filed: Dec. 22, 1989

Related U.S. Application Data

[63] Continuation-in-part of Ser. No. 369,479, Jun. 21, 1989.

[51] Int. Cl.⁵ .......................... C07K 15/28; C12N 5/00
[52] U.S. Cl. ..................................... 530/387; 530/388; 435/70.21; 435/172.2; 435/240.27; 935/106; 935/95
[58] Field of Search .................................. 935/95, 106; 530/387-388; 435/70.21, 172.2, 240.27

[56] References Cited

FOREIGN PATENT DOCUMENTS 230883A of 1985 Fed. Rep. of Germany ...................... 435/240.27

OTHER PUBLICATIONS

Cushley et al., Nature, vol. 298, 1982, pp. 577-579.
Whittler et al., Protein Engineering vol. 6, pp. 499-505.
Burnett, R. C. et al., "The IgA Heavy Chain Gene Family in Rabbit:Cloning & Sequence Analysis of 13 C-62 Genes", Embo Journal 8: 4041-47 (1989).
Robinson, E. A. et al., "Complete Amino Acid Sequence of a Mouse Immunoglobulin βChain (MOPC 511)", PNAS 11:4909-13 (1980).
Osborne, B. A. et al., "Evolution of the Genes", Dialog Database R65 Genetics 119:925-32 (1988).
Loghem, E. V. et al., "Allotypic and Isotypic Aspects of Human Immunoglobulin A", Molecular Immunology, vol. 20 (1983).
Word et al., "The Murine Immunoglobulin βGene Expresses Multiple Transcripts from a Unique Membrane Exam", (particularly; p. 895, 2nd col.), Embo Journal 2:887-898 (1983).
Blattner et al., Nature, vol. 307, 2 Feb. 1984, pp. 417-422.

Primary Examiner—Margaret Moskowitz
Assistant Examiner—Robert D. Budens
Attorney, Agent, or Firm—Eric P. Mirabel; Giulio A. DeConti, Jr.

[57] ABSTRACT

Antigenic epitopes associated with the extracellular segment of the domain which anchors immunoglobulins to the B cell membrane are disclosed. For IgA, the epitopes are present on IgA-bearing B cells but not the secreted, soluble form of IgA. The epitopes can be exploited for therapy and prophylaxis. For example, antibodies specific for the epitopes associated with the anchor and peptide encompassing the epitope domain of IgA can be used to increase secretory IgA production for the purposes of treating patients with infectious diseases and IgE-mediated allergic diseases.

2 Claims, 3 Drawing Sheets

```
   1 ctcccatccctcctaagcccaactaggacccaaagcatagacagggaggggccacgtgg
  61 ggtggcatcagaagCAGGCCAGTGAGACAGGGCCTGCCCAGGGCCCTCTGCATGCCTCTG
 121 GTTCTGCCTGGGCTCCCAGGAGTGTAAGAACAGTCCCACAACCACTGTGGGGACACCTGG
 181 CACTCAGACTCCCACAAGGGGGCAGTGGGGCCCCTGCTCGTGCCTTAGACATCTTCCGGG
 241 CCTCCCCAGGGCCCCCCGCCTTCTGGCTGCCTCCCTCTGCTCTCAGGGCCAAGGTGAGGT
 301 GGAGGCCACTGTCACCCCTGAGGGTCCAGTCACCAGAGGGTAATTGAGAGCAACAGGTCA
 361 CTCGGGGAAGCCCTGCCACAGAGAAGCCCTCCAGCCCATGGGACCCAGGACCTGGCCCAG
 421 GGGAGGGGCTTTTAAAGAGAGGGGGAAAGAGGGAGAATCAACAGATGAGGGGCTGAACCA
 481 GCAGACAGAGATCAGGCAGACACATGGGTAGATCCTAGGACATATAATGAATGGATGGGT
 541 GGATGGAGGATTGGTAGACGGAGGATGGATGGGTGGGTAAATGGCTGGATGGAGGATGGA
 601 CAGATGGATATATGATGGATGGATGAAGGACGGGTGGATGGAGGATGGATGAGTGGATGA
 661 ATGAAGGATGGAAGATGGATGGATGGATGGGTGGATGGACTGATGGATGATGGATGGATG
 721 GATGGATGGATGATGGATGGATGGGTAGGCGGATGGAGGATGGAAGGGTGGATGGAGGAT
 781 GGAAGATAGATGGAGGGGTGAATGGAGGATGGGTGGACTGACGGAGGATTGAGGATACTG
 841 GGGTGGGTGGGTGGGTAGATCTATGGAGGATAGGTGTATGGAAGATAATTGGATGGAGAA
 901 TTGCTTTATGAATGGATGAATGAAGAGATGGAAAATAGCTTTATAGATGGATGGGTGAAT
 961 GGATGGATGGATAGATGGAAGAAGGATGAATGGATGGAAAATAGCTTTATAGATATATGG
1021 GTGGATATTTAAGTGATAGCCTTACATTAATAGATGAATGGAGGATGAATGGTTGGGTGA
1081 GTGGGTAGGAGTGTTACTGATGGAGGGGTGGATATACGGATAATAGCTTTATAGATGGAT
1141 GGATGGATAGATGGATGGAAGGATAGAAAGACAGGTGAATGACTGGATGTATCAGCATAT
1201 GACAAGCAGGTACAGCTGTACATGGGAGGTCTATGCCCTGAGACCCTGAGGAAAATGAGG
1261 ATGCCCGTGCTGGTGGCCCTCACCTGGCCCTGCGTTGTAACCCCTCAGCCACATTCCCTG
1321 GGAAGGCAACAGAGGCCTCTGGTCTTGCCCATTCAACCTTTGGCACACTGAGTGTCAGAC
1381 CCAGTCTCTGTCTTGGACCCAGATCTCCTTGAGGGTGGGTGTGTCTGGTCCTCTCTGGCC
1441 CCGGGACCCAGTCACTGAATACGTGGCTGGGACTGAGACGGGGTGGGGTGGGAGGGGCGG
1501 GAGGGTACCTCGGGCTCAAGCTTCCCTTGGAGAAGCAGATGGTGTCCACTTTCTGCCCTG
1561 CCAAGTCTCTCCCTGAAGTGCCCTAAGAATGTCAAAGACAGAAGGTCCCAGCCCCTCACC
1621 TGGGACTCTGCCTCCTCATCCTCCCTGGGGAGTCTCAGGCCTTAGATGGGGACCCAGAC
1681 CCCACTGTCCCCAGACCCCAAGGAAGCATAGCCGCTGTTCACACGAGTCTGGGCTGGCA
1741 GCTCTTGCTCTGTTGCAGATTGGCAGATGCCGCCTCCCTATGTGGTGCTGGACTTGCCG
      g  s  c  s  v  a  D  W  Q  M  P  P  Y  V  V  L  D  L  P 1801 CAGGAGACCCTGGAGGAGGAGACCCCCGGCGCCAACCTGTGGCCCACCACCATCACCTTC
      Q  E  T  L  E  E  E  T  P  G  A  N  L  W  P  T  T  I  T  F 1861 CTCACCCTCTTCCTGCTGAGCCTGTTCTATAGCACAGCACTGACCGTGACCAGCGTCCGG
      L  T  L  F  L  L  S  L  F  Y  S  T  A  L  T  V  T  S  V  R 1921 GGCCCATCTGGCAACAGGGAGGGCCCCCAGTACTGAGCGGGAGCCGGCAAGGCACAGGTG
      G  P  S  G  N  R  E  G  P  Q  Y 1981 GGAGCCCAGGAGGGGGATGAGCCCACAGTGGATGAGGTGGGCTGCAGTGCTTGGCTAAGA
2041 GGAGAGCACCACCTGCTCCCACTGTGGGGGGACGTGCTCTCCTGGGGGGCCCTTCACAGA
2101 CACTGAGGACACGCGCAGGCCCAGGGTCAGGGCTGAGCTTCCCTCCAGTGCAGTAACGAG
2161 GATTCCGTCCAGGCTCCCATGAGCAGGCCAGGGCTGAGACAGAGGGCGTTGGCAAGGATG
2221 CTGCTCCTTCAGGCTGTGACCCCTCTGTCTTTGCAGGGAGGAAGTGTGGAGGAACCTCTT
2281 GGAGAAGCCAGCTATGCTTGCCAGAACTCAGCCCTTTCAGACGTCACCGACCCGCCCTTA
2341 CTCACATGCCTTCCAGGTGCAATAAAGTGGC
```

*Figure 1* gscsvaDWQMPPPYVVLDLPQETLEEEPGAN|LWPTTITFLTLFLISLFYSTALTVT|SVRGPSGNREGPQY mb/ec - α$_1$ | TRANSMEMBRANE PEPTIDE | CYTOPLASMIC PEPTIDE

Figure 2

```
              10            20            30            40
huα₁  — gscsvaDWQM  PPPYVVLDLP  QETLEEETPG  ANLWPTTITF
huα₂  — gsccvaDWQM  PPPYVVLDLP  QETLEEETPG  ANLWPTTITF
muα   — ------ERQE  PLSYVLLDQS  QDTLEEEAPG  ASLWPTTVTF 50            60            70
huα₁  — LTLFLISLFY  STALTVTSVR  GPSGNREGPQ  Y
huα₂  — LTLFLISLFY  STALTVTSVR  GPSGKREGPQ  Y
muα   — LTLFLISLFY  STALTVTTVR  GPFGSKEVPQ  Y
```

Figure 3

ANTIGENIC EPITOPES PRESENT ON MEMBRANE-BOUND BUT NOT SECRETED IGA

RELATED APPLICATIONS

This application is a continuation-in-part application of U.S. patent application Ser. No. 07/369,479, filed June 21, 1989.

BACKGROUND

Numerous pathogenic microorganisms, such as bacteria and viruses, enter the human and animal bodies through the respiratory, gastrointestinal, and genitourinary tracts during air inhalation, food and liquid intake, and sexual contact. The immune system has evolved to meet, in part, the needs of defending against these pathogens by the development of secretory IgA antibodies. IgA is produced by plasma cells located along the mucosal linings of these various tracts that are exposed to the external environment. The α chain and light chain immunoglobulins produced by plasma cells combine with a secretory component produced by the epithelial cells in the mucosal tissues, forming secretory IgA molecules that are secreted to the surface of mucosal layers. These IgA molecules bind to the invading pathogens and weaken their ability to penetrate the mucosal layer and to enter the inner tissue and blood stream of the hosts.

It is also well known that various allergic substances enter human and animal bodies through inhalation and food ingestion, causing immediate-type, antibody-mediated and delayed-type, cell-mediated hypersensitivities. The IgE-mediated reactions against pollens, animal danders, dust mites, and other allergic antigens cause common problems, such as hay fever (or allergic rhinitis) and extrinsic asthma among the sensitized individuals. In these allergic responses, the allergens enter the mucosal layers of the respiratory tracts and nasal linings and bind to allergen-specific IgE on the surface of mast cells. The cross-linking of IgE molecules by the allergens on the mast cell surface aggregates the underlying IgE Fc receptors, and trigger the release of histamine and other pharmacologic mediators, resulting in the various manifestations of allergic diseases. In the cell-mediated hypersensitivity, certain T helper cells responsible for delayed-type hypersensitivity are activated. These T cells recruit and activate macrophages, causing inflammatory symptoms.

In the two U.S. patent applications Ser. Nos. 229,178, filed Aug. 5, 1988 and 272,243, filed Nov. 16, 1988, the discovery of antigenic epitopes unique to membrane-bound but not secreted immunoglobulins was described. Antibodies specific for these epitopes can be used for the elimination of B cells producing the immunoglobulins. In particular, antibodies specific for the antigenic epitope locating in the transmembrane anchoring peptide of membrane-bound IgE can be used for the removal of IgE secreting B cells in patients suffering from IgE-mediated allergies.

Antibodies that belong to certain immunoglobulin classes and subclasses, such as murine $IgG_{2a}$ and human $IgG_1$, and that have appropriately high affinity for binding to surface antigens of target cells, can cause the specific lysis of the target cells. However, not all antibodies specific for target cells will cause cytolysis. The antibodies specific for various isotypes of immunoglobulins (anti-Ig antibodies) have been studied in numerous experiments to investigate the effects on B cells in vitro and in vivo. A broad range of effects, such as isotype switching, proliferation, increase or decrease of antibody production, have been reported. See Vitetta, E. D., et al., *Immunol. Rev.* 52:211–231 (1980); Cooper, M. D., et al., *Immunol. Rev.* 52:29–53 (1980). In numerous studies, polyclonal antibodies have been shown to induce B cell proliferation. See Sell, S. and Gell, P. G. H., *J. Exp. Med.* 122:423–44 (1965); Kishimoto, T., et al., *J. Immunol.* 115:1179–1184 (1975); Parker, D. C., *Nature* 258:361–363 (1975); Sieckmann, D. G., et al., *J. Exp. Med.* 147:814–829; Pure, E. and Vitetta, E. S., *J. Immunol.* 125:1240–1242 (1980). Unlike antibody-dependent cellular cytotoxicity and complement-mediated cytolysis, this proliferative response does not seem to involve the Fc of the antibodies, because F(ab')2 is more effective than whole antibody in inducing the proliferative effect. Vitetta, E. S. et al., *Immunol. Rev.* 52:211–231 (1980).

SUMMARY OF THE INVENTION

The invention pertain to the various therapeutic applications of peptidic segments that are the extracellular portions of the transmembrane anchoring peptides of membrane-bound immunoglobulins. These peptidic segments form entirely or partly the antigenic epitopes unique to membrane-bound but not secreted immunoglobulins. The peptide segment for human IgA has the amino acid sequence.

GSCS(or C)VADWQMPPPYVVLDLPQETLEEEP-GAN

Peptides having this sequence or an immunologically equivalent sequence (or a epitope thereof) can be conjugated to protein carriers and used to treat patients to modulate the synthesis of immunoglobulins, in particular, the increased synthesis of IgA. Antibodies specific for these antigenic epitopes, of certain immunoglobulin classes and subclasses, such as mouse $IgG_1$ or human $IgG_2$, or in the form of divalent antigen binding fragments such as F(ab')2, can also be used to enhance IgA synthesis. Further, peptides representing the IgM or IgD, or antibody specific for these peptides, can be used to stimulate IgA production. The peptides and antibodies can be used alone, or combined with vaccines, or allergenic antigens, to increase IgA synthesis. The patients populations include those susceptible to infectious diseases and those affected by allergic diseases.

BRIEF DESCRIPTION OF THE FIGURES

FIG. 1 shows the nucleotide sequence of the membrane exon (194 bp) and about 1,700 bp of the 5' flanking sequence and about 500 bp in the 3' untranslated region of the α1 subclass.

FIG. 2 shows the amino acid sequence of the extracellular portion of the transmembrane anchoring segment of the α subclass.

FIG. 3 shows the amino acid sequences of the membrane exons of human α1 and α2 and their comparisons with murine α1 and α2.

DETAILED DESCRIPTION OF THE INVENTION

1. Modulation of B Cell Activity by Antibodies Specific for Various Immunoglobulin Isotypes.

Owing mostly to the development of monoclonal antibody methodologies, the morphologically indistinguishable T lymphocytes are now known to contain functionally distinct subpopulations. Monoclonal antibodies specific for unique differentiation antigens of T cell subsets, such as CD3, CD4, CD8, etc., provide not only tools to identify the cells but also agents to modulate T cell activity in vitro and in vivo.

B lymphocytes produce five classes of immunoglobulins, which mediate different functions. IgM is most effective in complement fixation, IgG causes opsonization and cellular cytotoxicity and crosses placenta, IgA functions on the mucosal surface and IgE mediates degranulation of mast cells and basophils. The function of IgD is still not well understood. These antibodies are present in the blood circulation, with IgG, IgA, and IgM accounting for as major serum components. In addition to secreting immunoglobulins, the B cells also express one or more isotypes of immunoglobulins on the cell surface at different stages of maturation. IgM and IgD are present on the surface of resting, uncommitted B cells, while each of all five classes of immunoglobulins may exist on late stage, mature B cells, which are committed to secrete the same isotypes of immunoglobulins as expressed on the cell surface. Teale, J. M., et al., *J. Immunol.* 126:1952-1957 (1981); Gathings, W. E., et al., *Immunol. Rev.* 57:107-126 (1981); Teale, J. M., *Fed. Proc.* 41:5-9 (1982).

Numerous investigators have contributed a large body of literature on the studies of effects of anti-Ig antibodies on the activity of B cells. In the volume of review articles, "Effects of antiimmunoglobulin sera on B lymphocyte function", *Immunol. Rev.* Vol. 52, ed. by Moller, G. (1980), it was clear that anti-Ig antibodies have broad ranges of effects on B cells. Among those effects, the proliferative activities on B cells and the production of IgM, IgG and IgA were most extensively studied using anti-IgM and Anti-IgD antibodies. Anti-IgM and Anti-IgD antibodies appear to be able to switch the uncommitted B cells to producers of IgG and IgA. The conclusive findings from these studies are that the effects of anti-Ig antibodies to stimulate B cell proliferation require the divalency of the antibodies and involve the cross-linking of the surface Ig. The effects do not require Fc portions of the antibodies and, in fact, the F(ab')$_2$ fragments appear to be more effective than whole IgG in stimulating B cell proliferation.

The effects of anti-Ig antibodies on B cell proliferation would seem highly desirable for modulating B cell activity in vivo for enhancing antibody production. However, these effects are hardly attainable because of the very large concentrations of IgG, IgM, and IgA antibodies in the circulation. When anti-Ig antibodies are administered in vivo, they will bind to the circulating Ig before they can bind to significant amounts to the surface Ig on B cells. The present invention pertains to the development of antibodies that can be used to react with membrane-bound immunoglobulins to modulate B cell activity without reacting with secreted, circulating immunoglobulins.

2. IgA is Important for Immune Functions on Mucosal Surface

Some of the most common and serious infectious diseases, such as syphilis, AIDS, influenza, hepatitis B, are caused by pathogenic bacteria and viruses, that enter the human bodies through the respiratory, gastrointestinal, or genitourinary tracts. In much the same way that pathogenic microorganisms enter the airway of human respiratory system, the potentially allergic substances, such as tree, grass, or flower pollens, dust mites and fungal particles, animal danders, enter the human body.

The IgA antibody evolves for the defense at the mucosal surface against various foreign substances. IgA is synthesized by plasma cells found in higher densities near the linings of tracts that have exposure to the external environment. The IgA can bind to pathogenic mocroorganisms, weakening their ability to penetrate the mucosal layer to enter the inner tissue and blood stream. The IgA can also bind to allergenic substances, neutralizing or immobilizing the allergens to bind IgE or to activate T cells responsible for delayed-type hypersensitivity.

It has been found that individuals with deficiency of IgA production are more prone to various infectious diseases and have higher tendency to develop allergic diseases than those with normal IgA levels. These finding suggest that among those with susceptibility to contract infectious diseases and potential to develop allergic diseases, if the levels of either total IgA or antigen-specific IgA can be increased, the diseases may be prevented.

3. Anchoring Peptidic Piece of B Cell Membrane-bound Immunoglobulins

B cells express on their surface antibody molecules, which serve as receptors for antigens during immunological induction. The membrane-bound immunoglobulins differ from the secretory immunoglobulins synthesized by the same cells in that they have extra peptidic pieces that anchor the immunoglobulin molecules onto the cell surface.

The amino acid sequence data of the eleven membrane-bound immunoglobulins from several species have been determined. See Word, C. J. et al., *EMBO J.* 2:887-898 (1983); Ishida, N. et al., *EMBO J.*, 1:1117-1123 (1982); Steen, M. L. et al., *J. Mol. Biol.*, 177:19-32 (1984); Rogers, J. et al., *Cell*, 26:19-27 (1981); Yamawaki-Kataoka, Y. et al., *Proc. Natl. Acad. Sci., USA*, 79:2008-2012 (1982); Kamaromy, M. et al., *Nucleic Acids Res.*, 11:6775-6785 (1983); Rogers, J. et al., *Cell*, 20:303-312 (1980); Bernstein, K. E., *J. Immunol.* 132:490-495 (1984); Cheng, H. et al., *Nature* 296:410-415 (1982). These sequences indicate certain common features of the plasma membrane bound peptidic piece. As shown in Table 1, the peptidic anchor piece has three segments which are distinguishable based upon their locations in relation to the plasma membrane. Even though these peptidic pieces are short, ranging from 41 to 72 amino acid residues, and have often been referred to as the "membrane-bound domain", the peptides are not entirely in the membrane lipid bilayer. In fact, only 25 amino acid residues, largely hydrophobic residues and threonine and serine residues, located in the middle part of the peptides, are in the lipid bilayer. The C-terminal, hydrophilic segments of 3 to 28 amino acid residues are located on the cytoplasmic side of the membrane. The segments toward the N-terminus, which are connected to the third or fourth constant domains of the immunoglobulin heavy chains (CH$_3$ or CH$_4$) are very hydrophilic and are on the extracellular side of the plasma membrane.

TABLE 1

Key features and properties of peptidic segments unique to membrane-bound immunoglobulins on B cells.

| Immunoglobulin | First segment | Middle segment | Last segment | Total |
|---|---|---|---|---|
| | | Length | | |

TABLE 1-continued

Key features and properties of peptidic segments
unique to membrane-bound immunoglobulins on B cells.

| Class/Subclass | # Amino acid residues | | | |
|---|---|---|---|---|
| Mouse IgA | 26 | 25 | 14 | 65 |
| Mouse IgE | 19 | 25 | 28 | 72 |
| Rat IgE | 19 | 25 | 28 | 72 |
| Mouse IgG$_1$ | 18 | 25 | 28 | 71 |
| Mouse IgG$_{2a}$ | 18 | 25 | 28 | 71 |
| Mouse IgG$_{2b}$ | 18 | 25 | 28 | 71 |
| Mouse IgG$_3$ | 18 | 25 | 28 | 71 |
| Mouse IgM | 13 | 25 | 3 | 41 |
| Human IgM | 13 | 25 | 3 | 41 |
| Human IgD | 27 | 25 | 3 | 55 |
| Mouse IgD | 26 | 25 | 3 | 54 |
| Properties | Hydro-philic Highly acidic | Hydro-phobic No charged residues | Hydro-philic | |
| Physical Location | On exterior surface | In membrane lipid bilayer | On cytoplasmic surface | |
| Abbreviated Symbols | mb/ec segment | mb/tm segment | mb/ic segment | |

*mb for membrane-bound; ec for extracellular; tm for transmembrane; and ic for intracellular.

The shortest length of the extracellular segment of the membrane-bound pieces of the immunoglobulins (designated mb/ec segments) has 13 amino acid residues (mouse and human μ chains). See Table 2. The mb/ec segments of all immunoglobulins contain high proportions of charged amino acid residues, almost entirely acidic residues. The proportions of charged amino acid residues and polar hydrophilic residues account for very high percentages of the amino acid composition of the mb/ec segment (Table 3). These parameters indicate that all the mb/ec segments are exposed and long enough to be accessible by antibodies. The heavy chains evolved before the various mammals species, mice, rats, and humans evolved. Thus, among the various mb/ec segments that have been determined, it is probably the murine α-mb/ec that the human α-mb/ec, which sequence has not yet been reported, will be most related. The murine α.mb/ec has 26 amino acid residues, among them 5 Glu and 2 Asp residues. These data also provide support that human α-mb/ec segment is exposed and accessible to antibodies.

TABLE 2

The amino acid sequences of the exterior
portion of peptidic segments unique to
membrane-bound immunoglobulins (mb/ec segments).

| | Mb/ec segment | | | | | |
|---|---|---|---|---|---|---|
| | 26 | 21 | 16 | 11 | 6 | 1 |
| Mouse IgA | E | .RQEPL | .SYVLL | .DQSQD | .ILEEE | .APGAS |
| Mouse IgE | | | .ELDI | .QDLCI | .EEVEG | .EELEE |
| Rat IgE | | | ELDI | .QDLCT | .EEVEG | .EELEE |
| Mouse IgG$_1$ | | | GLQ | .LDETC | .AEAQD | .GELDG |
| Mouse IgG$_{2a}$ | | | GLD | .LDDVC | .AEAQD | .GELDG |
| Mouse IgG$_{2b}$ | | | GLD | .LDDIC | .AEAKD | .GELDG |
| Mouss IgG$_3$ | | | ELE | .LNGTC | .AEAQD | .GELDG |
| Mouse IgM | | | | EGE | .VNAEE | .EGFEN |
| Human IgM | | | | EGE | .VNAEE | .EGFEN |
| Human IgD | YL | .AMTPL | .IPQSK | .DENSD | .DYTTF | .DDVGS |
| Mouse IgD | I | .VNTIQ | .HSCIM | .DEQSD | .SYMDL | .EEENG |

TABLE 3

Composition of charged amino acid residues and
polar, hydrophilic amino acid residues in the exterior
portion of peptidic segments unique to membrane-bound
immunoglobulins (mb/ec segments).

| | TOTAL | Acidic residues | Basic residues | Polar residues | Total hydrophilic residues | Proportion of hydrophilic residues % |
|---|---|---|---|---|---|---|
| | | # Amino acid residues | | | | |
| Mouse IgA | 26 | 7 | 1 | 7 | 15 | 58 |
| Mouse IgE | 19 | 10 | 0 | 2 | 12 | 63 |
| Rat IgE | 19 | 10 | 0 | 2 | 12 | 63 |
| Mouse IgG$_1$ | 18 | 6 | 0 | 4 | 10 | 56 |
| Mouse IgG$_{2a}$ | 18 | 7 | 0 | 2 | 9 | 50 |
| Mouse IgG$_{2b}$ | 18 | 7 | 1 | 1 | 9 | 50 |
| Mouse IgG$_3$ | 18 | 6 | 0 | 4 | 10 | 56 |
| Mouse IgM | 13 | 6 | 0 | 2 | 8 | 61 |
| Human IgM | 13 | 6 | 0 | 2 | 8 | 61 |
| Human IgD | 27 | 6 | 1 | 8 | 15 | 56 |
| Mouse IgD | 26 | 7 | 0.5 | 9 | 16.5 | 63 |

Acidic residues: E (Glu), D (Asp)
Basic residues: K (Lys), R (Arg), H (His); His is partially charged.
Polar residues: S (Ser), T (Thr), C (Cys), Q (Gln), N (Asn)

4. Determining the amino acid sequence of mb/ec segment of human IgA(α-mb/ec segment).

The DNA sequence corresponding to the human α-mb/ec segment was determined as set forth in the exemplification below. The nucleotide sequence of the exon encoding the peptide segment and the amino acid sequence of the segment are shown in FIGS. 1 and 2.

The α-mb/ec peptides of this invention can comprise the amino acid sequence shown in FIG. 2, any immunologically active portion of the sequence or any epitopes contained in this sequence. In addition, the peptides include any modifications of the amino acid sequence of FIG. 2 in which amino acids have been added, inserted, deleted or substituted without detracting significantly from the immunological activity of the peptide. The immunological activity of the peptide includes reactivity with antibody and the ability (alone or conjugated to a carrier) to induce an immune response, including an antibody response, which is crossreactive with the α·mb/ec segment and native IgA on the cell membrane.

5. Developing Antibodies to mb/ec Segment.

The α·mb/ec peptide can be used in the immunization of animals to prepare polyclonal and monoclonal antibodies. They can also be used to screen for specific monoclonal antibodies or characterize specific polyclonal antibodies. They can also be used to purify monoclonal and polyclonal antibodies.

In the process of preparing for monoclonal antibodies specific for α·mb/ec peptide, it is not necessary to use the α·mb/ec peptide in both immunization and antibody identification. For example, in immunizing mice for preparing immune spleen cells for fusion with myeloma cells, the immunogen may be the membrane-bound IgA isolated from plasma membrane of IgA-bearing myeloma cells, such as DAKIKI lymphoblastoid cells. The immunogen may also be the IgA-bearing myeloma cells.

For using the synthetic α·mb/ec peptide for immunogen, it is more effective to conjugate the peptide to a protein carrier. A preferred protein carrier is keyhole lympit hemocyanin (KLH). If the peptidic segment lacks a Lys residue or if the Lys residue is in the middle part of the segment, it is desirable to add a Lys residue at the C-terminal end. Because the N-terminus already has an α-amino group, the modified synthetic peptidic will have two amino groups for linking.

Multiple molecules of peptides can be conjugated to each molecule of the carrier protein. With KLH, a preferred molar ratio for peptide/KLH is 10. The method of conjugation is very well established. Cross-linkers such as glutaldehyde or bis (sulfosuccinimidyl) suberate or disulfosuccinimidyl tartarate (Catalogue #21579, 20591, Pierce Chemical Co., Rockford, Ill.) have been used. A preferred cross-linker is the gluteraldehyde.

The immunogen, such as the KLH conjugate, can be used to immunize rabbits, goats, rats, or mice to prepare polyclonal antibodies specific for the α·mb/ec peptide. Lympocytes from the spleen or lymph nodes of immune mice and rats can also be taken to prepare hybridomas secreting monoclonal antibodies specific for the α·mb/ec peptide. A preferred protocol to prepare the monoclonal antibodies is to fuse immune spleen cells of mice with non-secreting mouse myeloma cells, such as NS-1 or SP2/0 cells using polyethylene glycol.

For optimal immunization of mice, 50 μg of the peptide-KLH conjugate in complete Fruend adjuvant is injected subcutaneously into each mouse for priming. Two and four weeks later, same amounts of antigen is given s.c. in incomplete Fruend adjuvant. At about the six week time point, the fourth antigen injection is given i.p. in saline. Mice are sacrificed 4 days after the last injection and the spleens are taken for preparing single cell suspension for fusion with myeloma cells. Similar protocol can also be used for immunization with purified native human membrane-bound IgA (having attached membrane anchor domain) isolated from the plasma membrane of IgA-bearing human myeloma cells, such as DAKIKI lymphoblastoid cells. When human IgA-bearing cells are used as the immunogen, $1 \times 10^7$ cells are injected i.p. with two week intervals.

The fusion procedure with polyethylene glycol and other various procedures concerning cloning and hybridoma culturing have been well established and the preferred protocol is the same as described by Hudson, L. and Hay. F. C. (Practical Immunology, 2nd edition, pp. 303-313, 1980, Blackwell Publishing Co., Boston).

The screening of hybridomas for monoclonal antibodies or the identification of polyclonal antibodies reactive with α·mb/ec peptide can be performed with enzyme linked immunosorbent assays (ELISA) using the synthetic α·mb/ec peptide as the solid phase antigen. An alternative solid phase antigen is the conjugate of α·mb/ec peptide with a different carrier protein such as bovine serum albumin different from that used in immunogen. Further characterization of the monoclonal and polyclonal antibodies are shown in Table 5. The assays employed in these studies are also indicated. The assays have been described in detail in the U.S. patent application Ser. No. 226,421, filed July 29, 1988, and U.S. patent application Ser. No. 140,036, filed Dec. 31, 1987, the teachings of which are incorporated by reference herein.

TABLE 5

The reactivity of antibodies specific for α.mb/ec peptide with different IgA-containing targets.

| | Reactivity | Assays |
| --- | --- | --- |
| Synthetic α.mb/ec peptide | + | ELISA |
| Soluble IgA | − | ELISA |
| DAKIKI myeloma cells | + | Immunofluorescence staining |
| IgA-bearing B cells | + | Immunofluorescence staining |
| Cells not expressing surface IgA | − | Immunofluorescence staining |

6. Experiments with Animal Models

The substances and methods are tested on animal model systems. A number of experiments are designed to investigate whether peptides representing ec/mb segments of various immunoglobulins and the antibodies specific for these antigenic epitopes will enhance the production of IgM, IgG, IgA, etc. in the animals. The peptides and antibodies relating to a particular isotype may have effects on the synthesis of several isotypes and subclasses. In the discussion below, we will primarily focus on peptides and antibodies relating to α·ec/mb segment. The purposes of the animal studies are to investigate;

a) Do the peptides and antibodies enhance antibody production?
b) Do the peptides and antibodies enhance secretory IgA production in the mucosal surface?
c) Can the peptides and antibodies be used prophylactically in preventing from infectious diseases?
e) Can the peptides and antibodies be used in patients with immunodeficiency diseases?
f) Can the peptides and antibodies be used in patients to prevent from or alleviate symptoms of allergic diseases?

Two of the most relevent systems are the following.
A. Primate model

The monoclonal antibodies specific for human α·mb/ec peptide and their related substances of this invention are tested to determine whether they react with IgA-bearing cells of rhesus monkeys.

A small portion of rhesus monkeys, which have been infected with the nematode, *Ascaris suum*, develop sensitivity to extract of ascaris. When these sensitive monkeys are given spray containing ascaris antigen, they develop breathing problems resembling asthma. Patterson, R., *J. Clini. Invest.* 57:586–593 (1976).

The various compositions of this invention can be examined in the asthma/rhesus monkey model system. The ascaris sensitive monkeys are given the experimental treatment or control treatment and measurements are made to determine:

(a) Does the asthma symptoms upon ascaris challenge decline?
(b) Does the circulating IgA increase?
(c) Does secretary IgA increase in pulmonary lavage?
(d) Does Ascaris antigen specific IgA increase?
(e) Does the circulating IgA-bearing B cells increase?

B. Mouse model system

The α-mb/ec segment of mouse has already been sequenced. Word, C. J. et al., *EMBO J.* 2:887–898 (1983). The 26 amino acid residue peptide is Glu-Arg-Gln-Glu-Pro-Leu-Ser-Tyr-Val-Leu-Leu-Asp-Gln-Ser-Gln-Asp-Ile-Leu-Glu-Glu-Glu-Ala-Pro-Gly-Ala-Ser.

The peptide is synthesized in several forms, including one that has extra Leu-Lys residues at the C-terminus.

The peptide and its KLH conjugate are used as antigens to immunize rabbits and goats. The antisera are collected. The antigen-specific antibodies are purified using column of Sepharose 4B conjugated with the peptide (with Leu-Lys addition) or with peptide linked to bovine serum albumin. Normal mice are injected i.v. or i.p. with the purified antibodies or their related substances. The mice may also be given α-ec/mb peptide-conjugated with LKH. They can also be immunized with a viral antigen, such as from rotavirus, combined with antibody or peptide treatment. The questions to be investigated are:

(a) Does the total IgA in circulation increase?
(b) Does total secretory IgA increase in the intestinal lumen?
(c) Does antigen-specific IgA increase?
(d) Does the number of IgA-bearing B cells in the spleen and Peyer's patches increase?
(e) Can the mice resist better the challenge with live virus?

7. Applications of α-ec/mb Peptide and Antibodies Specific for this Epitope in Infectious Diseases, Allergies, and Immunodeficiency Diseases The α-ec/mb peptide and antibodies specific for α-mb/ec epitopes can be used to increase total IgA, secretory IgA, or antigen-specific IgA in humans or other animals (e.g. dogs, cats and horses). The antibodies can be used therapeutically and prophylactically in several ways.

A. Antibodies specific for IgA-bearing cells

Antibodies of certain IgG subclasses, such as mouse IgG$_1$ and human IgG$_2$ and IgG$_4$, or F(ab')2 fragments may be used to achieve the purposes of enhancing antibody production. The antibodies can be administered as free antibodies to patients in amounts sufficient to induce proliferation of IgA-bearing B cells and, hence increase IgA production.

The antibodies can also be administered nasally. On the lining of nasal channel and respiratory tract are areas in which IgA-producing B cells reside in denser populations. It is possible that a nasal route of administration (e.g. by nasal spray) may be used to deliver relatively high concentrations of antibodies into these areas and thus to achieve speedier and more effective results. The antibodies can also be administered ocularly.

For therapeutic uses in humans, either human or chimeric (or "near-human") antibodies are preferred. Chimeric antibodies comprise a variable or antigen binding (hypervariable or complementarity determining) region derived from an animal antibody and the remaining regions derived from a human antibody. Methods for producing chimeric (e.g. murine/human) antibodies are well established. Chimeric antibodies can be produced in large quantities and they are less immunogenic in humans than nonhuman antibodies. Consequently, they are better suited for in vivo administration, especially when repeated or long term administration is necessary. Antibody fragments of the chimeric antibodies can also be used.

Immunotherapies employing the antibodies of this invention may be used in combination with conventional vaccination and desensitization immunotherapy. For example, desensitization with allergen may be performed in conjunction with the administration of anti-α-mb/ec antibodies.

B. α-mb/ec Peptide Analogues and Active Immunization Against α-mb/ec Epitope

Even though human α-mb/ec peptide is probably not immunogenic in humans, peptide with the same sequence and amino acid substitutions can be linked to carrier proteins, such as hepatitis B surface antigen or core antigen, and become immunogenic and capable to induce antibodies that cross react with authentic α-mb/ec epitope. The preferred peptides have the amino acid sequence GSCS(or C)VADWQMPPPYVVLDLPQETLEEEPGAN. Variants as described above can also be used. These α-mb/ec peptide analogues can be administered to patients susceptible to infectious diseases or IgE-mediated allergies. The antibodies induced by this active immunization can achieve the functions as the antibodies described in section A.

C. Antiidiotypic Antibodies and Methods of Active Immunization Against α-mb/ec Epitope.

The α-mb/ec-specific antibodies described thus far can be used to generate parotope-specific, anti-idiotypic antibodies which offer another mode of stimulating IgA production. Antibodies against the parotope of the α-mb/ec-specific antibodies conformationally resemble the epitope for which the anti-IgA antibody is specific, that is, they resemble an α-mb/ec epitope. These antiidiotypic antibodies (or fragments or peptides containing the antigen combining portions thereof) can be used to actively immunize against α-mb/ec and induce the endogenous formation of antibodies against the α-mb/ec epitope. The induced antibodies will mediate the various prophylactic and therapeutical effects of α-mb/ec-specific antibodies.

Because an α-mb/ec epitope is a "self-molecule", it is not immunogenic. However, active immunization against it may be achieved by using the parotope-specific antibodies of this invention. The parotope-specific antibody shares conformational resemblance with the antigen - the α-mb/ec epitope which can elicit immune response in humans against the epitope.

Paratope-specific, anti-idiotyptic antibodies are administered to a patient in an immunogenic amount to induce the formation of α-mb/ec antibodies. The antiidiotypic antibodies are preferably administered as chimeric antibodies. They may also be given as antibody fragments (which also may be chimeric in nature).

8. Diagnostic Uses

Antibodies against α-mb/ec epitopes can be used to identify and enumerate IgA-bearing lymphocytes in mixed leukocyte populations. For this purpose, antibodies can be used in standard assay formats for determining cell surface antigens. In general, the antibody is contacted with a sample of the leukocytes to be tested under conditions which allow the antibody to bind IgA-bearing cells in the sample. The cells are then examined for binding of antibody. This can be accomplished by conventional cell staining procedures. For example, a fluorescently labeled second antibody can be used to detect binding of the anti-IgA antibody.

EXEMPLIFICATION

Methods

DNA library and probe. The human genomic DNA library was purchased from Stratagene (LaJolla, Calif.). This library was constructed using genomic DNA from human lung fibroblast line, W138, packaged in phage FIX. A 30-base oligonucleotide 5'GCGAGAAG-TACCTGACTTGGGCATCCCGGC3'(Oligo. #1), which corresponds to a segment located in the CH3 coding region of immunoglobulin allotype α1 and α2, was synthesized and used as a probe to screen phage clones containing either α1 or α2 gene segments using in situ hybridization.

Polymerase chain reaction (PCR). To amplify genomic DNA segments, the purified DNA from the positive clones was used as the templates. One primer was a 17-base oligonucleotide, 5'CTGCCTGGCCAAGTCTC3'(Oligo. #2), located in the intron about 1 kb downstream from CH3 exon, and the other primer was a 21-base oligonucleotide, 5'GAACAAGCTCAGTAGGAAGAG3'(Oligo. #3), which is a very conservative segment in the published mouse o membrane exon (Word et al. EMBO J. 2:887, 1983). To amplify cDNA spanning human CH3 and the membrane exon, purified cDNA reverse transcribed from mRNA from a surface IgA-expressing cell line (see below) was used as the template. One primer was the same 30-base oligonucleotide (#1) located in CH3 exon used in genomic library screening, and the other primer was an 18-base oligonucleotide, 5'GCTCCCGCTCAGTACTGG3'(Oligo. #4), which is located at the junction of human α membrane exon and the 3' untranslated region. The PCR was carried out in DNA Thermal Cycler (Perkin Elmer Cetus) and the reaction conditions were: denaturing at 94° for 1 min, annealing at 50° for 2 min, reacting with Taq polymerase (Perkin Elmer Cetus) at 72° for 5 min genomic DNA or 45 sec for cDNA. The reaction cycles were 30 for genomic DNA and 40 for cDNA.

Cloning and sequencing. The products from PCR were extracted with phenol and the DNA was precipitated with ethanol. The newly synthesized DNA segments were blunted by Mung Bean nuclease (United States Biochemicals) and their 5' ends were phosphorylated by polynucleotide kinase (New England Biolabs). The amplified DNA fragments of interest were isolated by agarose gel electrophoresis and ligated into plasmid pUC19 (United States Biochemicals) at the restriction site of Sma 1. After transforming into E. coli DH5α (Bethesda Research Laboratories), the amplified plasmids were purified using CIRCLEPREP kit (BIO101). DNA sequences of the inserts were determined by the method of dideoxy sequencing on double stranded DNA with T7 Sequencing kit (Pharmacia). The membrane exon regions were sequenced on both strands of DNA to minimize errors. An additional step was performed for identifying clones containing inserts of α gene segment amplified by PCR from cDNA. The colonies were hybridized with an oligonucleotide probe of 22 nucleotides, 5'CCTCCCTATGTGGTGCT-GGACT3' (Olig. #5, segment #1774–1795 in FIG. 1), located between the two primers used in PCR.

Southern blot and subclone. As described above, the first genomic DNA segment used for sequencing was obtained by PCR amplification using two primers, the 3'-end primer of which was in the middle of the membrane exon. In order to obtain sequences for the remaining 3'-end of the membrane exon and the 3' untranslated region, gene segments containing these regions were prepared. Purified genomic DNA's from clones containing human α1 or α2 segments were digested with restriction enzyme Ava 1, electrophoresed on 1% agarose gel, and blotted onto nitrocellulose filter according to the standard Southern blot method. A $^{32}$P labelled oligonucleotide located in the membrane exon mentioned above (Oligo. #5) was used as a probe to identify DNA fragments containing segments neighboring the oligonucleotide probe. The positive segments were then isolated and subcloned into pUC 19 at the restriction site of Ava 1 and sequenced downstream using the same oligonucleotide used in Southern blot analysis.

RNA and cDNA preparation. A mIgA-expressing cell line, DAKIKI (ATCC TIB206), was used as the source of mRNA. About $5 \times 10^7$ cells were harvested for isolation of total RNA using guanidinium procedure. With the purified RNA as the template, an oligonucleotide at the end of membrane exon as the primer (Oliga #4), the first strand cDNA was polymerized by the reverse transcriptase AMV (life Science, Inc.) according to the procedure in the provided instruction manual.

Results

PCR amplification of α1 and α2 gene segment from genomic DNA and their nucleotide sequence. Nine phase lambda clones containing human α1 or α2 heavy chain gene segments were identified from the human genomic library. These clones were used directly as the template for PCR with Oligo. #2 and Oligo. #3 as primers. The 5' end primer (Oligo #2) for the PCR was selected from a segment identical between human α1 or α2 genes located near the 3' end of the published genomic DNA sequences, which ends in an intron about 1.1 kb downstream from CH3. Flanagen, J. G., et al. Cell 36:681–688 (1984). Whether the genes belonging to α1 or α2 subclasses can be distinguished by subclass-specific sequences immediately downstream from the Oligo. #2 primer. Both α1 or α2 membrane gene segments were identified among our nine lambda genomic clones. Through agarose gel electrophoresis, the products of PCR were separated into 3 bands of DNA segments, 2 major bands of 1.8 kb and 300 bp, respectively, and a minor band of 2.2 kb. The 1.8 kb segment was thought the segment of interest judging by the size of the corresponding segment in the already sequenced murine αgene. This DNA segment was purified from the agarose gel, subcloned, and sequenced.

The sequence of this 1.8 kb fragment indicated that on its 3' end there was a segment of about 120 bp with sequence sharing very high homology with that of murine α membrane exon. A possible splicing acceptor sequence, 5'TTGCAGA3', was identified near the 5' end of this 120 bp segment. Since the 1.8 kp fragment ends in the middle of the membrane exon, the sequences for the remaining membrane exon and the 3' untranslated region were obtained by subcloning and sequencing of additional lambda clones containing segments flanking the membrane exons. These clones were identified by Southern blot analysis using a probe (Oliga. 5) from the membrane exon.

The sequence of the membrane exon (194 bp) and about 1.700 bp of 5' flanking sequence and about 500 bp in the 3' untranslated region of $\alpha 1$ subclass is shown in FIG. 1. The sequence indicates that the stop codon TGA is at exactly the same site as that of a murine $\alpha$ membrane exon, making the human and mouse $\alpha$ membrane exons equal in length of 194 nucleotides. At about 400 dp downsteam from the membrane exon, there is a possible mRNA termination and polyadenylation signal sequence, 5'AATAAA3'. Like the murine $\alpha$ gene, the human $\alpha$ genes have only one membrane exon, while all other classes of human or murine heavy chain genes with known sequences have two membrane exons. The intron between CH3 and the membrane exon has 2,579 bp, somewhat longer than the 2,350 bp of murine. In this intron, there is a region of about 630 bp, in which only a few C bases and more than 20 repeated sequences of 5'GGATGGA3' and other repeated sequences exist. The significance of that is unknown.

PCR and DNA sequencing on cDNA. As mentioned above, we located the human $\alpha$ membrane exon by comparing the sequence of the segment amplified from genomic DNA with that of murine $\alpha$ membrane exon as well as by searching for the splicing acceptor consensus sequence. A segment of 194 necleotides (from nucleotide #1760 to #1953 in FIG. 1) was originally thought to be the membrane exon. To confirm this, we isolated the total RNA from a human mIgA-expressing cell line, DAKIKI, and prepared its cDNA. With this cDNA as template, a segment spanning CH3 and membrane exon was amplified by PCR. Although we increased the PCR cycles from 30 to 40, the efficiency of amplification was still not as good as that of PCR on genomic DNA, probably because of the relative lower proportion of the specific template of interest in the cDNA prepared from the total RNA. On agarose gel electrophoresis, the PCR products displayed a weak band of the right size with a heavy smear around it. This band was cut out and subcloned. To help identifying the specific clones, in situ colony hybridization was performed using a probe located between the two primers of PCR. Positive clones were picked up, purified and sequenced using the same method as that of genomic DNA.

The results showed that there were clones containing DNA inserts which corresponds to two species of mRNA of human membrane-bound $\alpha 1$. The two mRNA species results from the use of two different splicing acceptor sites: one from the predicated site, 5'TTGCAGA3' which corresponding site existed in the murine $\alpha$ gene; and one from an acceptor site, 5'TGGCAGG3' 18 nucleotides upstream in the same reading frame and there is not a corresponding site in the murine $\alpha$ gene (the slashes indicate the cleavage/splicing sites). The two mRNA species would yield two membrane-bound $\alpha 1$, polypeptides, one with 65 and the other with 71 amino acid residues in the transmembrane anchor peptide region (FIGS. 1 and 2). These two mRNA species and their corresponding $\alpha 1$ peptides are referred to as isoforms. As shown in FIGS. 1 and 2, the 6 extra amino acid residues in isoform 2 (the longer) are indicated by lower case letters. The extracellular segments of the transmembrane peptides of either 25 or 31 amino acid residues (mb/ec-$\alpha 1$) contain high proportions of acidic residues. These mb/ec-$\alpha$ segments are the target antigenic epitopes for antibody-based treatments. FIG. 3 shows the DNA and amino acid sequences of the membrane exons of human $\alpha 1$ and $\alpha 2$ and their comparisons with the murine $\alpha 1$ and $\alpha 2$ and they are highly homologous to murine $\alpha$. The mb/ec-$\alpha$ peptides are identical between $\alpha 1$ and $\alpha 2$ for isoform 1 and have only one amino acid residue with isoform 2.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A chimeric antibody which binds specifically to human IgA on the surface of B-cells, but does not bind to secreted, soluble IgA, the antibody having a murine antigen binding region and a human heavy chain constant region.

2. A chimeric antibody of claim 1, which binds to the extra cellular segment of the membrane-bound domain of IgA.

* * * * *